United States Patent
Troczynski et al.

(10) Patent No.: US 6,730,324 B2
(45) Date of Patent: May 4, 2004

(54) BIOFUNCTIONAL HYDROXYAPATITE COATINGS AND MICROSPHERES FOR IN-SITU DRUG ENCAPSULATION

(75) Inventors: Tomasz Troczynski, Vancouver (CA); Dean-Mo Liu, Richmond (CA); Quanzu Yang, Vancouver (CA)

(73) Assignee: The University of British Columbia, Vancouver (CA)

( * ) Notice: Subject to any disclaimer, the term of this patent is extended or adjusted under 35 U.S.C. 154(b) by 38 days.

(21) Appl. No.: 09/838,331

(22) Filed: Apr. 20, 2001

(65) Prior Publication Data

US 2002/0155144 A1 Oct. 24, 2002

(51) Int. Cl.$^7$ ................................................. A61K 9/14
(52) U.S. Cl. ........................ 424/489; 424/400; 424/490; 424/497
(58) Field of Search ............................... 424/400, 489, 424/497, 490

(56) References Cited

U.S. PATENT DOCUMENTS

| | | |
|---|---|---|
| 5,055,307 A | 10/1991 | Tsuru et al. |
| 5,525,148 A | 6/1996 | Chow et al. |
| 5,958,430 A | 9/1999 | Campbell et al. |
| 5,993,535 A | 11/1999 | Sawamura et al. |

FOREIGN PATENT DOCUMENTS

| | | |
|---|---|---|
| WO | WO98/16209 | 4/1998 |
| WO | WO98/16268 | 4/1998 |
| WO | WO00/23123 | 4/2000 |

OTHER PUBLICATIONS

Y. Shinto, et al., Calcium Hydroxyapatite Ceramic Used as a Delivery System for Antibiotics, *Journal of Bone and Joint Surgery*, vol. 74-B, No. 4, Jul. 1992.

T.W. Bauer, et al., Hydroxyapatite-Coated Femoral Stems, *Journal of Bone and Joint Surgery*, vol. 73-A, No. 10, Dec. 1991, 1439–1452.

K. Ohkouchi, et al., Disposition of Anticancer Drugs after Bolus Arterial Administration in a Tissue-isolated Tumor Perfusion System, *Cancer Research* 50, 1640–1644, Mar. 1, 1990.

H. Imoto, et al., Disposition Characteristics of Macromolecules in the Perfused Tissue-isolated Tumor Preparation, *Cancer Research* 52, 4396–4401, Aug. 15, 1992.

R.W. Evans, et al., Cultured Human Monocytes and Fibroblasts Solubilize Calcium Phosphate Crystals, *Calif. Tissue Int.* (1984) 36:645–650.

L.L. Hench, Bioceramics: From Concept to Clinic, *J. Am. Ceram. Soc.* 74(7):1487–510 (1991).

K. Hwang, et al., Sol–gel derived hydroxyapatite films on alumina substrates, *Surface and Coatings Technology* 123 (2000) 252–255.

M. Otsuka, et al., A Novel Skeletal Drug Delivery System Using Self-Setting Calcium Phos-phate Cement. 7. Effect of Biological Factors on Indomethacin Release from the Cement Loaded on Bovine Bone, *Journal of Pharmaceutical Sciences*, vol. 83, No. 11, Nov. 1994.

P. W. Brown, et al., Variations in Solution Chemistry During Low-Temperature Formation of Hydroxyapatite, 1848–1854.

E. Fernandez, et al., Calcium phosphate bone cements for clinical applications: Part I: Solution chemistry, *Journal of Materials Science: Materials in Medicine* 10, (1999) 169–176.

M. Itokazu, et al., Synthesis of antibiotic-loaded interporous hydroxyapatite blocks by vacuum method and in vitro drug release testing, *Biomaterials* 19 (1998) 817–819.

S.A. Bender, et al., Effect of protein on the dissolution of HA coatings, *Biomaterials* 21 (2000) 299–305.

M. Otsuka, et al., A novel skeletal drug delivery system using self-setting calcium phosphate cement VIII: the relationship between in vitro and vivo drug release from indomethacin-containing cement, *Journal of Controlled Release* 43 (1997) 115–122.

M. Otsuka, et al., A Novel Skeletal Drug-Delivery system Using Self-Setting Calcium Phosphate Cement 3. Physiochemical Properties and Drug-Release Rate of Bovine Insulin and Bovine Albumin. *Journal of Pharmaceutical Sciences*, vol. 83, No. 2, Feb. 1994.

I. Soriano and C. Evora, Formulatino of calcium phosphates/poly (d,l–lactide) blends containing gentamin for bone implantation, *Journal of Controlled Release* 68 (2000) 121–134.

B.R. Constantz, et al., Skeletal Repair by in Situ Formation of the Mineral Phase of Bone, *Science*, vol. 267, Mar. 24, 1995, 1796–1799.

P. Layrolle and A. Lebugle, Synthesis in Pure Ethanol and Characterization of Nanosized Calcium Phosphate Fluoroapatite, *Chem. Mater.* 1996, 8, 134–144.

(List continued on next page.)

*Primary Examiner*—Thurman K. Page
*Assistant Examiner*—Amy E Pilliam
(74) *Attorney, Agent, or Firm*—Oyen Wiggs Green & Mutala (57) ABSTRACT

This invention relates to novel room-temperature process for obtaining calcium phosphate, in particular hydroxyapatite, coatings and microspheres that encapsulate drugs, proteins, genes, DNA for therapeutical use. The coatings and microspheres are designed to perform a defined biological function related to drug delivery, such as gene therapy through gene delivery. A novel method for encapsulation, and subsequent controlled release of therapeutically active agents from such biofunctional coatings and microspheres is disclosed. Such coatings and microspheres are useful for side-effects free, long-term, targeted, controlled release and delivery of drugs, proteins, DNA, and other therapeutic agents.

13 Claims, 8 Drawing Sheets

OTHER PUBLICATIONS

P. Layrolle and A. Lebugle, Characterization and Reactivity of Nanosized Calcium Phosphates Prepared in Anhydrous Ethanol, *Chem. Mater.* 1994, 6, 1996–2004.

M. Ohtsuka, et al., Effect of Plasma–calcium–level–responsive Oestradiol Release from Apatitic Bone Cement on Bone Mineral Density in Ovariectomized Rats, *J. Pharm. Pharmacol*: 1999, 51:475–581.

M. Ohtsuka, et al., Oestradiol Release from Self–setting Apatitic Bone Cement Responsive to Plasma–calcium Level in Ovariectomized Rats, and its Physiochemical Mechanism, *J. Pharm. Pharmacol*. 1997, 49:1182–1188.

D. Cohn and H. Younes, Biodegradable PEO/PLA block copolymers, *J. Biomedical Materials, Research*, vol. 22, 993–1009 (1988).

O. Bermudez, et al., Development of some calcium phosphate cements from combinations of α–TCP, MCPM and CaO, *J. Materials Science: Materials in Medicine*, 5(1994) 160–163.

M. Vert, et al., Biochemistry and biocompatibility of aliphatic polyesters, *J. Materials Science: Materials in Medicine*, 3(1992) 432–446.

C.C.P.M. Verheyen, et al., Evaluation of hydroxyapatite/poly(L–lactide) composites: physico–chemical properties, *J. Materials Science: Materials in Medicine* 4(1993) 58–65.

D.B. Haddow, et al., Characterization of sol–gel surfaces for biomedical applications, *J. Materials Science: Materials in Medicine* 7(1996) 255–260.

T. Li, et al., Hydroxyapatite coating by dipping method and bone bonding strength, *J. Materials Science: Materials in Medicine* 7(1996) 355–357.

K.A. Gross, et al., Thin hydroxyapatite coatings via sol–gel synthesis, *J. Materials Science: Materials in Medicine* 9(1998) 839–843.

L.D. Piveteau, et al., Thin films of calcium phosphate and titanium dioxide by a sol–gel route: a new method for coating medical implants, *J. Materials Science: Materials in Medicine* 10(1999), 161–167.

I. Khairoun, et al., Incorporation of a controlled–release glass into a calcium phosphate cement, *J. Materials Science: Materials in Medicine* 10(1999) 215–218.

C.S. Chai and B. Ben–Nissan, Bioactive nanocrystalline sol–gel hydroxyapatite coatings, *J. Materials Science: Materials in Medicine* 10(1999) 465–469.

A. Jillavenkatesa and R.A. Condrate, Sr., Sol–gel processing of hydroxyapatite, *J. Materials Science* 33 (1998) 4111–4119.

A. Jillavenkatesa, et al., An electron microscopy study of the formation of hydroxyapatite through sol–gel processing, *J. Materials Science* 34 (1999) 4821–4830.

C. S. Chai, et al., Critical ageing of hydroxyapatite sol–gel solutions, *Biomaterials* 19 (1998) 2291–2296.

M. Otsuka, et al., Antibiotic delivery system using bioactive bone cement consisting of Bis–GMA/TEGDMA resin and bioactive glass ceramics, *Biomaterials* 18 (1997) 1559–1564.

B. Mavis and A. Cuneyt Tax, Dip coating of Calcium Hydroxyapatite on Ti–6A1–4V Substrates, *J. Am. Ceram. Soc.* 83 (4) 989–991 (2000).

S.W. Russell, et al., Chemical and Structural Evolution of Sol–Gel–Derived Hydroxyapatite Thin Films under Rapid Thermal Processing, *J. Am. Ceram.* 79 (4) 837–842 (1996).

F.H. Westheimer, et al., Rates and Mechanisms of Hydrolysis of Esters of Phosphorous Acid, *J. Am. Chem. Soc.* 1988, 110, 181–185.

P. Layrolle, et al., Sol–Gel Synthesis of Amorphous Calcium Phosphate and Sintering into Microporous Hydroxyapatite Bioceramics, *J. Am. Ceram. Soc.* 81 (6) 1421–1428 (1998).

D.B. Haddow and P.F. James, Sol–Gel Derived Calcium Phosphate Coatings for Biomedical Applications, *J. of Sol–Gel Science and Technology* 13, 261–265 (1998).

J–C. Schrotter, et al., Silicon and Phosphorus Alkoxide Mixture: Sol–Gel Study by Spectroscopic Technics, *J. Sol–Gel Science and Technology* 4, 195–204 (1995).

Q. Qiu, et al., Bone Growth on Sol–Gel Calcium Phosphate Thin Films in Vitro, *Cells and Materials*, vol. 3, No. 4, 1993, 351–360.

M. Otsuka, et al., Calcium–level responsive controlled drug delivery from implant dosage forms to treat osteoporosis in an animal model, *Advanced Drug Delivery Reviews* 42 (2000) 249–258.

K.Z. Zhu, et al., Preparation, Characterization, and Properties of Polyactice (PLA)–Poly(ethylene Glycol) (PEG) Copolymers: A Potential Drug Carrier, *J. Applied Polymer Science*, vol. 39, 1–9 (1990).

J. Livage, et al., Sol–gel synthesis of phosphates, *J. Non–Crystalline Solids* 147&148 (1992) 18–23.

S. Kaciulis, et al., XPS study of apatite–based coatings prepared by sol–gel technique, *Applied Surface Science* 151 (1999) 1–5.

H. Takahashi, et al., synthesis of stoichiometric hydroxyapatite by a "Gel" route from the aqueous solution of citric and phosphonacetic acids, *Eur. J. Solid State Inorg. Chem.* t.32, 1995, 829–835.

Y. Masuda, et al., Synthesis of Hydroxyapatite from Metal Alkoxides through Sol–Gel Tech–nique, *J. Gea.Soc. Japan* 98 1266–1277, 1990.

W. Weng, et al., The Alkoxide Sol–Gel Process in the Calcium Phosphate System and its Applications, *Applied Organometallic Chemistry* 13, 555–564 (1999).

F. Minguez, et al., Post–Antibiotic Effect of Isepamicin Comparedto that of Other Aminoglycosides, *Drugs Exptl. Clin. Res.* XVI(5) 231–235 (1990).

H.B. Wen, et al., Preparation of calcium phosphate coatings on titanium implant materials by simple chemistry, *J. Biobed. Mater. Res.* 41, 227–236 (1998).

H.B. Wen, et al., Fast precipatation of calcium phosphate layers on titanium induced by simple chemical treatments, *Biomaterials* 1997, vol. 18, No. 22, 1471–1478.

H–M. Kim, et al., Thin film of low–crystalline calcium phosphate apatite formed at low tempera–ture, *Biomaterials* 21 (2000) 1129–1134.

M. Otsuka, et al., Effect of geometrical cement size on in vitro and in vivo indomethacin release from self–setting apatite cement, *Journal of Controlled Release* 52 (1998) 281–289.

D.–M Liu and I–W. Chen, Encapsulation of Protein Molecules in Transparent Porous Silica Matrices Via an Aqueous Colloidal Sol–Gel Process, *Acta mater.* vol. 47, No. 18, 4535–4544 (1999).

L.M. Ellerby, et al., Encapsulation of Proteins in Transparent Porous Silicate Glasses Prepared by the Sol–Gel Method, *Science*, vol. 255, Feb. 28, 1992, 1113–1115.

C. Ohtsuki, et al., Mechanism of apatite formation on $CaO-SiO_2-P_2O_5$ glasses in a simulated body fluid, *Journal of Non–Crystalline Solids* 143 (1992) 84–92.

E. Kon, et al., Autologous bone marrow stromal cells loaded onto porous hydroxyapatite ceramic accelerate bone repair in critical–size defects of sheep long bones, *J. Biomed. Mat. Res.* 49, 328–337 (2000).

F.C.M. Driessens, et al., Formulation and setting times of some calcium othophosphate cements: a pilot study, *Journal of Materials Science: Materials in Medicine* 4 (1993) 503–508.

Y.Abe, et al., Apatite coatings on ceramics, metals and polymers utilizing a biological process, *Materials in Medicine* 1 (1990) 233–238.

F.C.M. Driessens, et al., Effective formulations for the preparation of calcium phosphate bone cements, *Journal of Materials Science: Materials in Medicine* 5 (1994) 164–170.

D.M. Liu, et al., Plasma–sprayed hydroxyapatite coatings: effect of different calcium phosphate ceramics, *Journal of Materials Science: Materials in Medicine* 5 (1994) 147–153.

K. de Groot, et al., Plasma sprayed coatings of hydroxyapatite, *Journal of Biomedical Materials Research*, vol. 21, 1375–1381 (1987).

K. Yamamura, et al., Synthesis of antibiotic–loaded hydroxyapatite beads and in vitro drug release testing, *Journal of Biomedical Materials Research*, vol. 26, 1053–1064 (1992).

M. Otsuka, et al., A Novel Skeletal Drug–Delivery System Using Self–Setting Calcium Phos–phate Cement. 4. Effects of the Mixing Solution Volume on the Drug–Release Rate of Heteroge–neous Aspirin–Loaded Cement, *Journal of Pharmaceutical Sciences*, vol. 83, No. 2., Feb. 1994, 259–263.

M. Otsuka, et al., A Novel Skeletal Drug Delivery System Using Self–Setting Calcium Phos–phate Cement. 2. Physiochemical Properties and Drug Release Rate of the Cement–Containing Indomethacin, *Journal of Pharmaceutical Sciences*, vol. 83, No. 5, May 1994, 611–615.

A.A. Campbell, et al., Surface–induced mineralization: A new method for producing calcium phosphate coatings, *Journal of Biomedical Materials Research*, vol. 32, 111–118 (1996).

W. Paul, and C.P. Sharma, Development of porous spherical hydroxyapatite granules: applica–tion towards protein delivery, *Journal of Materials Science: Materials in Medicine* 10 (1999) 383–388.

M. Diarra, et al., Elaboration and evaluation of an intraoral controlled release delivering system, *Biomaterials* 19 (1998) 1523–1527.

Y. Tabata, The importance of drug delivery systems in tissue engineering, *PSST*, vol. 3, No. 3, Mar. 2000, 80–89.

C. Hamanishi, et al., Self–setting, bioactive, and biodegradable TTCP–DCPD apatite cement, *Journal of Biomedical Materials Research*, vol. 32, 383–389 (1996).

O. Bermudez, et al., Optimization of a calcium orthophosphate cement formulation occurring in the combination of mnocalcium phosphate monohydrate with calcium oxide, *Journal of Materials Science: Materials in Medicine*, 5 (1994) 67–71.

Y. Takakura, et al., Development of gene drug delivery systems based on pharamcokinetic studies, *European Journal of Pharmaceutical Sciences* 13 (2001) 71–76.

Spray Gun → 　Slurry Mix: CPC powder + liquid + Drug

Warm Air (~40C)

Microsphere Collector

To Stage 1: microsphere setting (Fig. 3b)

BIOFUNCTIONAL HYDROXYAPATITE COATINGS AND MICROSPHERES FOR IN-SITU DRUG ENCAPSULATION

TECHNICAL FIELD

This invention relates to novel room-temperature process for obtaining calcium phosphate, in particular hydroxyapatite, microspheres and coatings with encapsulated drugs, proteins, genes, DNA for therapeutical use. The coatings and microspheres are designed to perform a defined biological function related to drug delivery, such as gene therapy through gene delivery. A novel method for encapsulation, and subsequent controlled release of therapeutically active agents from such biofunctional coatings and microspheres is disclosed. Such coatings and microspheres are useful for side effects-free, long-term, targeted, controlled release and delivery of drugs, proteins, DNA, and other therapeutic agents.

BACKGROUND OF THE INVENTION

Rapid progress in the human genome project promises that diseases that could not be treated before can be curable in near future. The expectation is that the trial-and-error era of fighting illnesses by addressing the symptoms is coming to an end. Consequently, the issue of drug and gene release control becomes increasingly critical. Currently, many types of new drugs, or genes, have to be administered by daily injections, or even several times per day. An entirely new approach to drug delivery is therefore necessary to fully utilize the advantages of new drugs resulting from the genome project. Slow but steady release of drugs is sought in treatment of many diseases, from cancer and Parkinson's disease, to hormonal treatment of obesity where directly administered hormones reside in human body only for short period of time. In the past, polymeric materials have been used for drug delivery control and enjoyed substantial clinical success for certain drug systems. The need for alternative inorganic drug delivery systems, offering more flexibility in drug-carrier system selection, bioresorption and release control, hydrophobic/hydrophilic property control, and negligible side effects, is just emerging. Hydroxyapatite (HA) matrix for drug encapsulation, being already the principal inorganic component of bone, offers entirely new perspectives for drug delivery systems.

Hydroxyapatite Ceramics, $Ca_{10}(PO_4)_6(OH)_2$, belong to a large class of calcium phosphate (CaP) based bioactive materials used for a variety of biomedical applications, including matrices for drug release control [M. Itokazu et al Biomaterials, 19,817–819,1998; F. Minguez et al Drugs Exp. Clin. Res., 16[5], 231–235, 1990; W. Paul and C. P. Sharma, J. Mater. Sci. Mater. Med., 10, 383–388,1999]. Other members of the CaP family, such as dicalcium phosphate $CaHPO_4 2H_2O$ or tricalcium phosphate $Ca_3(PO_4)_2$, have also been used for similar purposes. The CaP family of materials has been long recognized as having highest degree of biocompatibility with human tissue.

Calcium Phosphate Cements (CPC) were reported in a binary system containing tetracalcium phosphate (TTCP) and dicalcium phosphate anhydrate (DCPA) [L. C. Chow et al. J. Dent Res., 63, 200,1984]. The CPC advantages of self-setting and apatitic phase, e.g. HA, as an end product led to applications such as bone replacements and reconstruction, and also drug delivery [M. Dairra, et al. Biomaterials, 19 1523–1527, 1998; M. Otsuka, et al. J. of Controlled Release 43(1997)115–122, 1997; Y. Tabata, PSTT, Vol.3, No.3, 80–89, 2000; M. Otsuka, et al. J. of Pharm. Sci. Vol.83, No.5, 1994]. CPC is typically formulated as a mixture of solid and liquid components in pertinent proportions, which react to form the apatite. The physicochemical reactions that occur upon mixing of the solid and liquid components are complex, but dissolution and precipitation are the primarily mechanisms responsible for the final apatite formation [C. Hamanish et al J. Biomed. Mat. Res., Vol.32, 383–389,1996; E. Ferandez et al J. Mater. Sci.Med.10,223–230, 1999]. The reaction pathway in most CPC systems does not lead to stoichiometric HA, but rather calcium-deficient $Ca_{10-x}(HPO_4)_x(PO_4)_{6-x}(OH)_{2-x}$, similar to that found in bone. The process parameters, such as Ca/P ratio, powder/liquid ratio, seeds concentration and type, nature of reagents, control the final properties, such as phase content, porosity, strength, setting time, phase transformation kinetics, and microstructure of CPC-derived hydroxyapatite (CPC-HA). Bermudez et al [J. Mat. Sci. Med. 4, 503–508,1993; ibid 5, 67–71, 1994] correlated the compressive strength of CPC vs starting Ca/P ratio in the systems of monocalcium phosphate monohydrate (MCPM) and calcium oxide. The optimum Ca/P ratio was found in a range of 1.25–1.45. Brown et al. [J. Am. Cerm. Soc. 74[5] 934-40,1991] found that the kinetics of HA formation at low temperatures in DCP/TTCP system are initially controlled by the surface area of the reactants, and eventually by diffusion. These process variables will be used in the present project to control crystallinity, and thus resorption and drug release rate from the HA microspheres.

Biomimetic Deposition of HA films at room temperature (BM-HA) was used for a variety of biomedical applications, including drug delivery [H. B. Wen et al, J. Biomed. Mater. Res., 41, 227–36,1998; S. Lin and A. A. Campbell, U.S. Pat. No. 5,958,430, 1999; D. M. Liu et al J. Mater. Sci. Mater. Med., 5, 147–153,1994; K. de Groot et al, J. Biomed. Mater. Res., 21, 1375–1381,1987]. This forming mechanism is driven by supersaturation of $Ca^{2+}$ and $PO_4^{3-}$, under appropriate solution pH, where HA is the most stable phase. The apatitic crystals form through nucleation and growth, and may incorporate biologically active species, such as antibiotics, anti-cancer drugs, anti-inflammatory agents, etc. The deposition rates are however small for BM-HA, generally in the range of 0.05–0.5 $\mu$m/h, and high concentration dosage of drug is difficult to achieve. Therefore, stand-alone BM-HA is not suitable if the goal is to form films in excess of 1 $\mu$m, but may be appropriate as an additional encapsulating film, on top of the porous HA structure saturated with the drug material. This is especially critical for orthopedics where high concentration of antibiotics is required at bone-HA interface to prevent acute inflammation in early after-operation stages. Furthermore, the physiological solutions for BM-HA formation are naturally water-based, which makes impossible to encapsulate hydrophobic bioactive agents into BM-HA coatings.

Sol-Gel Deposition of HA (SG-HA) films at elevated temperatures (375–500° C.) was disclosed previously by D. Liu and T. Troczynski in U.S. patent application Ser. No. 09/563,231, filed May 2, 2000, the subject matter of which is incorporated herein by reference. Sol-gel (SG) processing of HA allows molecular-level mixing of the calcium and phosphor precursors, which improves chemical homogeneity of the resulting calcium phosphate. The versatility of the SG method opens an opportunity to form thin film coatings in a simple, mild, relatively low-temperature process. The crystallinity of the calcium phosphate phase obtained through the novel inventive process by D. Liu and T. Troczynski can be enhanced by appropriate use of water treatment during processing. Variation of Ca/P ratio in the sol-gel precursor mix allows one to obtain other than calcium phosphate phases, for example, hydroxyapatite, dicalcium phosphate, tricalcium phosphate or tetracalcium phosphate. The use of SG-HA thin (<1 $\mu$m) dense highly crystalline films to nucleate and grow thick (>10 $\mu$m) CPC-HA porous, low-crystallinity (amorphous) films for drug encapsulation and release is hereby disclosed.

Problems With Drug Delivery in Vivo are related to toxicity of the carrier agent, the generally low loading capacity for drugs as well as the aim to control drug delivery resulting in self-regulated, timed release. With the exception of colloidal carrier systems, which support relatively high loading capacity for drugs, most systems deliver inadequate levels of bioactive drugs. In terms of gene delivery, to date the most efficient, though least safe methods of delivery are through viral mediated gene transfer. It is highly inefficient method, and is faced with even greater problems than the delivery of drugs due to the hydrophilic and labile nature DNA oligos. The problems with delivery of genes or antisense oligos originate from the rapid clearance of plasmid DNA or oligos by hepatic and renal uptake as well as the degradation of DNA by serum nucleases [Takura Y, et al. Eur. J. Pharm. Sci. 13 (2001) 71–76]. These effects have been observed for both in situ and intravenous delivery. For example it was estimated that more than half of the intravenous or in situ delivered naked plasmid DNA was cleared from the tumor site within the first two hours following intratumoral injection [Ohkouchi, K., et al Cancer Res. 50, (1996) 1640–1644 and Imoto, H., et al. Cancer Res. 52, (1992), 4396–4401]. Even after clearance, only a small percentage of the remaining DNA or oligos make their way to the cytoplasm or nucleus of the target cell. The membrane permeability of naked DNA and especially oligos is virtually nonexistent, due to their polyanionic nature. For this reason, their uptake through the endosomal compartment is associated with a severe drop in pH and degradation. Finally, many of the genes delivered have to be transported and sometimes incorporated in the genome of the target cell for stable expression. This makes very difficult gene transfer in vivo. In addition, successful controlled release is still problematic as for most applications (with the exception of naked DNA vaccines) it is desirable to have a prolonged expression of the gene of interest to ameliorate a particular medical condition. In most applications anywhere from a few weeks to several months are desired for the expression of a certain gene product.

Drug Encapsulation in HA has been achieved in the past by simple post-impregnation of a sintered, porous HA ceramic [K. Yamamura et al, J. Biomed. Mater. Res., 26, 1053–64,1992]. In this process, the drug molecules simply adsorb onto surface of the porous ceramic. The drug release is accomplished through desorption and leaching and the drug to the surrounding tissue after exposure to physiological fluid. Unfortunately, most of the adsorbed drug molecules release from such system in a relatively short period of time. Impregnation of drug material into porous sintered calcium phosphate microspheres has been reported in patent literature. "Slow release" porous granules are claimed in U.S. Pat. No. 5,055,307 [S. Tsuru et al, 1991], wherein the granule is sintered at 200–1400 C and the drug component impregnated into its porosity. "Calcium phosphate microcarriers and microspheres" are claimed in WO 98/43558 by B. Starling et al [1998], wherein hollow microspheres are sintered and impregnated with drugs for slow release. D. Lee et al claim poorly crystalline apatite [WO98/16209] wherein macro-shapes harden and may simultaneously encapsulate drug material for slow release. It has been suggested to use porous, composite HA as a carrier for gentamicin sulfate (GS), an aminoglycoside antibiotic to treat bacterial infections at infected osseous sites [J. M. Rogers-Foy et al, J. Inv. Surgery 12 (1997) 263–275]. The presence of proteins in HA coatings did not affect the dissolution properties of either calcium or phosphorus ions and that it was solely dependent on the media [Bender S. A. et al. Biomaterials 21 (2000) 299–305].

The group of Kobe University lead by Prof. M. Otsuka performed series of investigations of drug encapsulation in self-setting calcium phosphate cements derived from tetracalcium phosphate and dicalcium phosphate [J. Contr. Rel. 43 115–122 1997; ibid 52 281–289 1998; J. Pharm. Sci. 83 611–615, 259–263, 255–258, 1994]. The cement was shaped with in-situ drug encapsulation, into 15 mm diameter macropellets and drug (indomethacin) release monitored over up to 3 weeks period. It was concluded that the cement-drug delivery system, shaped in-situ into surrounding bone tissue, may be an excellent way to treat localized bone infections with high therapeutic effectiveness. The advantage of HA for drug delivery is that side effects have never been a concern for hydroxyapatite materials [Y. Shinto et al, J. Bone Jt. Surg., 74B4, 600–4,1992]. Calcium phosphate—biodegradable polymer blends were also investigated as possible vehicles for drug delivery [I. Soriano and C. Evora, J. Contr. Rel. 68 121–134 2000]. Prolonged drug release (up to 10 weeks) was obtained for the composites coated with hydrophobic polymer coatings. A group from University of Pennsylvania [Q. Qiu et al J. Biomed Mat Res. 52 66–76 2000] recently processed polymer-bioactive glass-ceramic composite microspheres for drug delivery. Porous calcium phosphate ceramics were impregnated with bone marrow cells [E. Kon et al, J. Biomed Mat. Res. 49 328–337 2000] and with human bone morphogenetic protein [I. Alam et al J. Biomed Mat. Res. 52 2000].

S. Takenori et al., in U.S. Pat. No. 5,993,535 (and accompanying EP0899247), disclosed a calcium phosphate cement comprising tetracalcium phosphate and calcium hydrogen phosphate polysaccharide as main components. It needed 24 hours incubation at 37° C. for conversion of hydroxyapatite. T. Sumiaki et al., in U.S. Pat. No. 5,055,307, disclosed slow release drug delivery granules comprising porous granules of a calcium phosphate compound having a ratio of Ca to P of 1.3 to 1.8, a porosity of 0.1 to 70%, a specific surface area of 0.1 to 50 m$^2$/g and a pore size of 1 nm to 10 $\mu$m. The granules were fired at a temperature of 200 to 1400° C., and a drug component impregnated in pores of the granules, and a process for producing the same. S. Gogolewski, in WO00/23123, disclosed the hardenable ceramic hydraulic cement comprising a drug to be delivered to the human or animal body upon degradation or dissolution of the hardened cement. However, conversion of CPC to achieve HA needed 40 hours. L. Chow et al., in U.S. Pat. No. 5,525,148, disclosed calcium phosphate cements, which self-harden substantially to hydroxyapatite at ambient temperature when in contact with an aqueous medium. More specifically the cements comprise a combination of calcium phosphates other than tetracalcium phosphate with an aqueous solution adjusted with a base to maintain a pH of about 12.5 or above and having sufficient dissolved phosphate salt to yield a solution mixture with phosphate concentration equal to or greater than about 0.2 mol/L. However, major disadvantages of the processing are that high pH (>12.5), which could denature most of drugs, proteins and DNA, so the process is not suitable for drug encapsulation vehicles. C. Rey et al., in WO9816209, disclosed a synthetic, poorly crystalline apatite calcium phosphate containing a biologically active agent and/or cells, preferably tissue-forming or tissue-degrading cells, useful for a variety of in vivo and in vitro applications, including drug delivery, tissue growth and osseous augmentation. However, the ratio of Ca/P was limited less than 1.5, and the authors did not disclose how to fabricate the microspheres and coatings.

The physical characteristics, i.e. shape, of the hydroxyapatite ceramic, also have significant impact on the tissue response. Among different possible shapes, hydroxyapatite granules facilitate not only surgical operations but also benefit the tissue growth after implantation by creating relatively large inter-granular pores allowing invasion by the host tissue. On this basis, the use of drug-containing HA granules has enhanced therapeutic effect in practical clinical/biomedical applications.

While the above studies describe the dissolution of porous HA to release a soluble extracellular acting bioactive ingredient through desorption and leaching, this disclosure aims also intracellular delivery of genes, drugs or proteins using resorbing HA microcarriers. The key observation is that HA particles were found inside macrophages at the interface of HA-coated hip implants [Bauer T. W. et al. J. Bone Joint Surg. Am. 73-A (1991) 1439–1452]. Consequently it was proposed that phagocytes take up and solubilize HA particles [Evans R. W. et al. Calcif. Tissue. Int. 36 (1984) 645–650]. This may be therefore one of the principal mechanisms of intracellular delivery of genes through use of HA coatings and microspheres, without the need for use viral mediated gene transfer.

SUMMARY OF INVENTION

We hereby disclose a process through which hydroxyapatite can be engineered to function as an efficient vehicle for drug delivery from coatings or self-supported microspheres. The process relates to calcium phosphate (CaP), in particular hydroxyapatite (HA) microspheres and coatings capable to encapsulate any type of drug or protein which can be dispersed in organic liquids or water. The process starts with calcium phosphate cement (CPC) slurry, followed by incubation to precipitate HA phase within the microsphere or within the coating. By adding drugs and proteins into colloidal suspension (CPC slurry) of the microsphere or coating precursors, a direct, in-situ encapsulation, and subsequent controlled release of the therapeutically active agents from the apatite microspheres is achieved. The varying degree of crystallinity of the microspheres is used to control and customize their resorption process in body fluids, and thus the rate of drug release.

Despite the fact that several techniques were investigated in the past in use of static macro-components of CaP for drug delivery, none of them allows processing of fast setting functionally gradient cement microspheres and coatings with in-situ drug encapsulation. Consequently we disclose hereby a new, safe and inexpensive way to deliver drugs, proteins, genes and antisense oligos in vivo. In this process calcium phosphate coatings and microspheres are obtained through dissolution-precipitation mechanism similar to setting of calcium phosphate cements (CPC). This process is used for deposition of adhesive, thick (typically of 10–1000 $\mu$m thickness) HA films and for making HA microspheres (typically of 10–1000 $\mu$m diameter).

Calcium phosphate cements, like most other cements (e.g. Portland cement) release heat of hydration when hydrating and setting. When setting fast (which is an important requirement in certain applications), this heat may not dissipate fast enough and temperature of cemented area increases, sometimes to a level high enough to damage, e.g. crack, the cement. More importantly, if the cement is applied in human body, e.g. as part of an implant, this temperature increase may damage the surrounding biological constituents such as cells, proteins, and enzymes when the heat is rapidly dissipated upon setting. The novel cement system disclosed here, experiences a relatively mild temperature rise during setting, i.e. from room temperature, ~20° C., to a maximum near body temperature, ~37° C. This cement also exhibits excellent mechanical properties. For example, its compressive strength is generally greater than 10 MPa, and in certain compositions, >30 MPa.

This CPC slurry is a mixture of acidic calcium phosphates, such as monocalcium phosphate (MCP) anhydrate or dihydrate, and basic calcium hydroxide, together with a small amount of other inorganic ingredients, such as apatite seeds. This mixture is thoroughly mixed, e.g. using ball milling. The mixture, which is suspended in an inert liquid medium (e.g. alcohols) or a liquid mixture of the inert medium and a small amount of phosphating liquid, has a starting Ca/P ratio in the range of 1.2–1.67 and a solid concentration of 30–70 vol %, before the shaping process is being carried out (i.e. filling the cavity with the cement or shaping a drug-impregnated microsphere). The shaping procedures can be optimized upon control of the setting time within 2–40 minutes.

The resulting cement exhibits an apatitic phase (HA) with either an acicular grain or plate-like grain morphology, depending upon processing parameters. A nano-structured cement can also be synthesized and is used particularly for encapsulating drugs, antibiotics, proteins, and enzymes. The apatite phase develops within 1–6 h of incubation within the CPC system disclosed. Fast formation of the apatite phase is advantageous for an early biological response with the surrounding host tissue. A fast setting (2–40 min) and hardening time (less than 6 hours) benefits enormously clinical applications of the cement. Controllable crystallinity, from amorphous (easily resorbable) to highly crystalline (i.e. stable in physiological environment), of the final apatitic structure allows application-oriented customization of the cement. Fine (nano-to-submicron) starting ingredients allow final microstructure to be well controlled, allowing high strength of the final body. Nano-structure of the novel CPC offers great advantage for encapsulating drugs, as well as for their controlled release. Apatite microspheres can be easily fabricated using the novel CPC formulation, with size ranging from 10–1000 microns, using simple spray-drying equipment. Control of the setting and hardening process of the cement microspheres allows a variety of biomedical or clinical applications, e.g., injection-packing, and in-situ hardening for repair, restoration, augmentation of defective tissues, and many others.

The disclosed process can be utilized to synthesize HA ceramics of different physical forms, at room temperatures. The following applications are targeted: granules or bulk shapes for artificial bone filler/bone reconstruction; room-temperature processed coatings (on Ti and other alloys), with drug incorporation; organic/inorganic composites, including HA in combination with other materials such as biopolymers and ceramics, and proteins to form nano- and bio-composites with controlled drug release function and/or bone growth control functions.

We disclose here a novel approach to achieve a multi-layer, functionally gradient HA coatings or microspheres. That is, several layers of HA coatings are deposited using different techniques, with different functions assigned to any particular layer. In particular, we describe an in-situ drug encapsulation within the functionally gradient HA coatings processed by combining elevated-temperature sol-gel processing with room-temperature precipitation processing. As a result of this protocol, a 10–30 µm thick, nano-to-submicron porous HA matrix, firmly attached to a metallic substrate through a 0.6–0.8 µm thin intermediate HA film is achieved. The thin sol-gel HA film (SG-HA) develops good bond with the underlaying substrate at the 400 C. processing temperature, and acts as an intermediate nucleation/bonding layer between the underlying substrate and the HA thick film matrix. The CPC-HA thick film matrix is deposited at room-temperature on the thin SG-HA film by dip coating in non-aqueous suspension of monocalcium phosphate and calcium hydroxide precursor powders. The drug material is dispersed in the suspension and initially deposited within the pores of the precursor powder film. Subsequently, a porous thick film apatite is formed under physiological environment, through dissolution-precipitation process. The thin SG-HA film acts as a seeding template allowing nucleation and growth of the thick film apatite crystals, and therefore imparts sufficient interfacial strength to the HA matrix. This room-temperature coating process, associated with an in-situ encapsulation of drugs, can be applied onto variety of metallic or non-metallic substrates, providing potential advantages in various biomedical/biochemical applications.

The microspheres are self-supporting granules produced through spray-drying and incubation process of CPC-HA precursors slurry, using sythesis routes and chemistry much the same as for the coatings. Further details of the invention are provided below.

A room-temperature process for deposition of adhesive, thick hydroxyapatite films on metallic substrates through dissolution-precipitation mechanism similar to setting of calcium phosphate cements (CPC) is disclosed. Such nanoporous, semi-amorphous 10–1000 µm thick film is rapidly grown on the underlying crystalline thin film of hydroxyapatite deposited through sol-gel process. A direct, in-situ encapsulation, and subsequent controlled release of therapeutically active agents from the apatite coatings has been achieved. Slight modification of similar process leads to formation of medicated HA microspheres of 10–1000 µm diameter. Both the coatings and microspheres are designated for side-effects free, long-term, targeted, controlled release and delivery of drugs, proteins, DNA, and others.

The invention is directed to a process for preparing a calcium phosphate phase which comprises: (a) dispersing a homogenization of monocalcium phosphate $Ca(H_2PO_4)_2$ and calcium hydroxide $Ca(OH)_2$ precursors in a substantially water-free medium to form a paste or viscous slurry of precursors; (b) drying the precursors slurry; (c) admixing a water-based solution of phosphate ions in the slurry to produce a mixture; and (d) incubating the resulting mixture in a humid environment at a temperature of 20–50° C. to dissolve the precursors and precipitate a calcium phosphate phase.

The calcium phosphate phase can be hydroxyapatite. The Ca/P atomic ratio in the precursors mixture can be in the range of 1.2–1.67 and the mixture can have a solids concentration of 30–70 vol %. The substantially water-free medium can be an alcohol. The alcohol can be ethyl alcohol, methyl alcohol or propyl alcohol. The water-based solution of phosphate ions can be sodium phosphate and the humid environment can be 50% to 100% Relative Humidity.

The precursors slurry can be dried in a prescribed shape. The shape can be a pellet, a coating, a microsphere, or a dental cavity or bone cavity fill. A crystalline hydroxyapatite powder can be added to the precursors slurry to promote crystallization of hydroxyapatite calcium phosphate phase during the incubation period. A therapeutically active material can be added to the precursors slurry for encapsulation during crystallization of the hydroxyapatite calcium phosphate phase during the incubation period. The therapeutically active material can be a drug, a protein, a gene or DNA.

The slurry of precursors can be deposited and dried on the surface of a calcium phosphate substrate. The calcium phosphate substrate can be a thin film of hydroxyapatite coating deposited on a metallic substrate using sol-gel process. The precipitated calcium phosphate phase can be exposed to a solution supersaturated with $Ca^{2+}$ and $PO_4^{3-}$ ions to provide a coating of biomimetic hydroxyapatite film on the precipitated calcium phosphate phase.

The slurry of precursors can be atomized and spray-dried to obtain microspheres of the precursors. The microspheres of the precursors can be exposed to a water-based solution of phosphate ions and incubated in a humid environment at a temperature of 20–50° C. to promote dissolution of the precursors and precipitation of calcium phosphate phase. The microsphere containing the precipitated calcium phosphate phase can be exposed to a solution supersaturated with $Ca^{2+}$ and $PO_4^{3-}$ ions to provide a coating of biomimetic hydroxyapatite film on the precipitated calcium phosphate phase. The precipitated calcium phosphate phase can be exposed to a solution polymer to form a polymer film on the microsphere surface.

BRIEF DESCRIPTION OF DRAWINGS

In drawings which illustrate specific embodiments of the invention, but which should not be construed as restricting the spirit or scope of the invention in any way.

DETAILED DESCRIPTION OF INVENTION

Figure 1A:
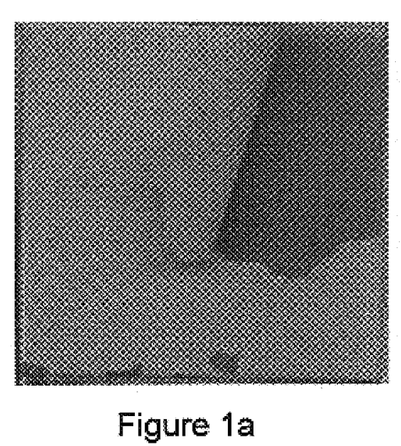
FIG. 1(a) illustrates a CPC-HA coating on a metallic substrate without SG-HA coating interlayer.
Figure 1B:
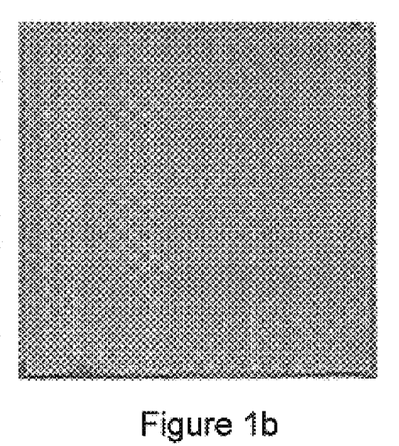
FIG. 1(b) illustrates a CPC-HA coating on a metallic substrate with SG-HA coating.
Figure 2A:
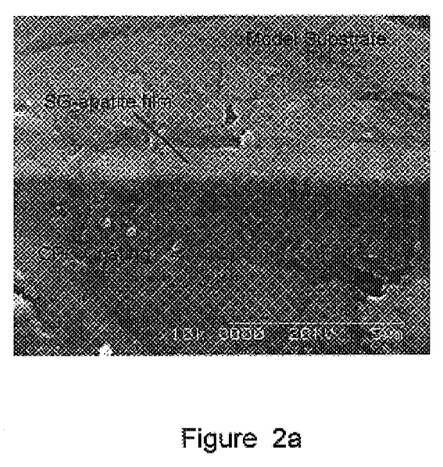
FIG. 2(a) illustrates a cross-sectional view of the CPC-HA/SG-HA coating system.
Figure 2B:
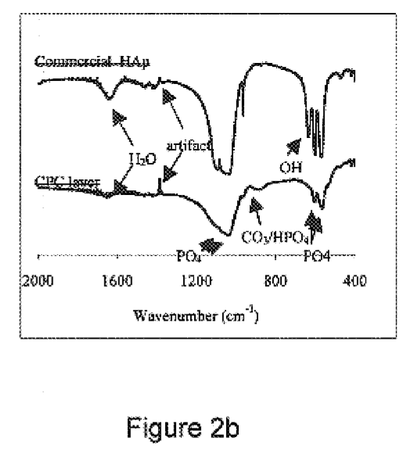
FIG. 2(b) illustrates a FTIR spectrum of the CPC-HA/SG-HA coating system.

In order to produce the thick HA films for drug encapsulation, surface of the underlying substrate (typically stainless steel or titanium) is first coated with thin, submicrometer film of sol-gel HA, as disclosed previously in U.S. patent application Ser. No. 09/563,231, filed May 2, 2000, the subject matter of which is incorporated herein by reference. The thin sol-gel HA film (SG-HA) develops good bond with the underlying substrate at the 400° C. processing temperature, and acts as an intermediate nucleation and bonding layer between the underlying substrate and the CPC-HA thick film matrix. The CPC-HA thick film matrix is deposited at room-temperature on the thin SG-HA film by dip coating in non-aqueous suspension of monocalcium phosphate and calcium hydroxide precursor powders. The drug material is dispersed in the suspension and initially deposited within the pores of the precursor powder film. Subsequently, the precursor powders film, containing drug material, is exposed to water-based solution of sodium phosphate and placed in an incubator at 37° C., 100% relative humidity, for up to 24 h. During this period, a porous thick HA film forms due to dissolution of the precursor powders and re-precipitation of apatite phase encapsulating the drug material. The thin SG-HA film acts as a seeding template allowing nucleation and growth of the thick film apatite crystals, and therefore imparts sufficient interfacial strength to the HA matrix. As a result of this protocol, a 10–1000 μm thick, nano-to-submicron porous CPC-HA matrix encapsulating the drug material, firmly attached to a substrate through a 0.6–0.8 μm thin intermediate SG-HA film is achieved. FIG. 1 illustrates CPC-HA coating on metallic substrates (a) without SG-HA coating interlayer and (b) with SG-HA coating. Absence of the SG-HA coating interlayer causes spontaneous separation of CPC-HA coating from the substrate. FIG. 2 shows cross-sectional view of the CPC-HA/SG-HA coating system (a) and its FTIR spectrum (b) compared with commercial crystalline hydroxyapatite. An excellent, intimate interface between the two films of CPC-HA/SG-HA coating system confirms that SG-HA acts as a nucleation site for CPC-HA.

Figure 3A:
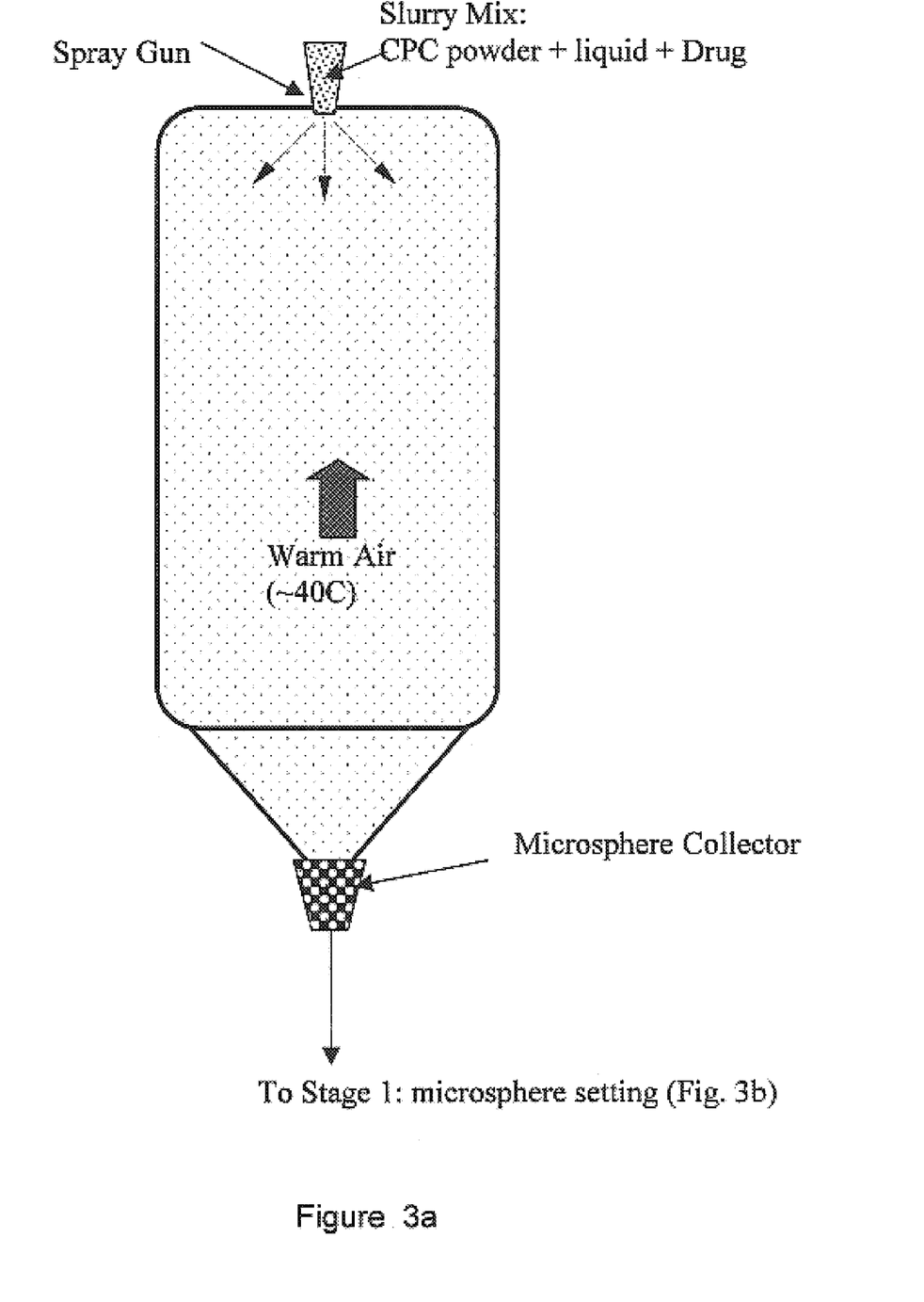
FIG. 3(a) illustrates a schematic of a spray-drying system for CPC microspheres for drug encapsulation.
Figure 3B:
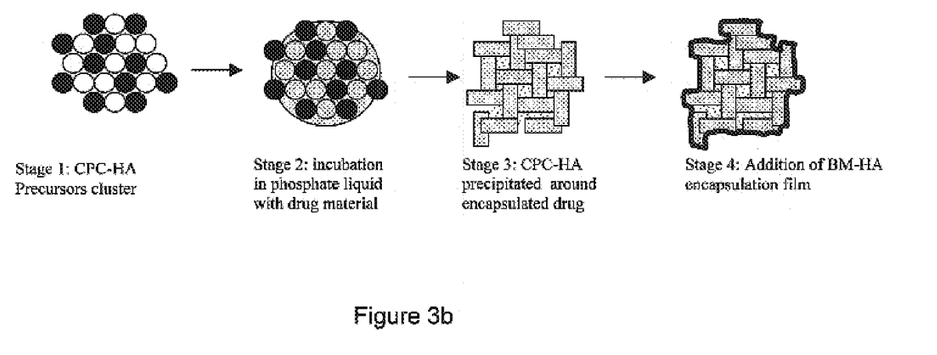
FIG. 3 illustrates the four stages of CPC-HA microsphere processing.
Figure 4A:
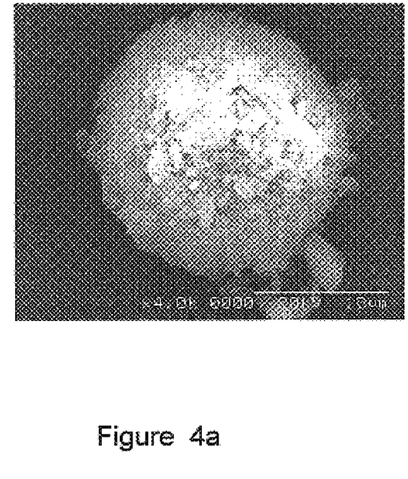
FIG. 4(a) illustrates CPC-HA microspheres, ~20 µm large.
Figure 4B:
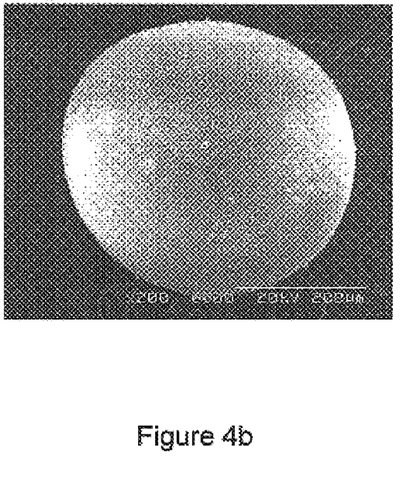
FIG. 4(b) illustrates CPC-HA microspheres ~300 µm large.
Figure 5A:
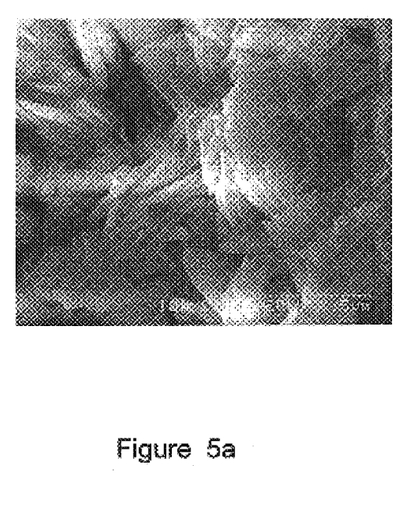
FIGS. 5(a) and 5(b) illustrate respective CPC-HA microstructure: crystalline (a) and amorphous (b).
Figure 5B:
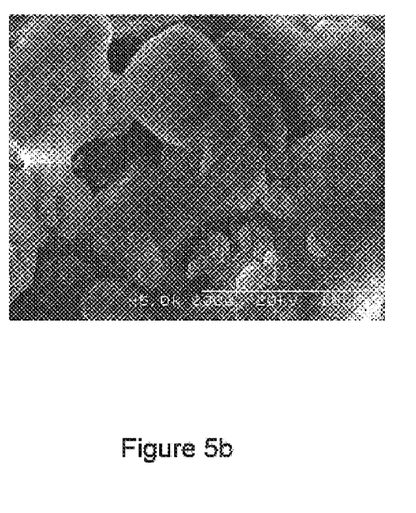

In order to produce the HA microspheres for drug encapsulation, the non-aqueous suspension of CPC precursor powders (monocalcium phosphate and calcium hydroxide), together with fine crystalline HA additive seeds, is atomized and spray dried to produce 10–1000 μm large approximately spherical particles (FIG. 3a, and Stage 1 in the schematic FIG. 3). The drug material is dispersed in the suspension and initially deposited within the pores of the precursor powder microspheres. Subsequently, the precursor powders microspheres, containing drug material, are exposed to water-based solution of sodium phosphate and placed in an incubator at 37° C., 100% relative humidity, for up to 24 h (Stage 2). During this period, a porous HA microsphere forms due to dissolution of the precursor powders and re-precipitation of apatite phase encapsulating the drug material, Stage 3. The fine crystalline HA additive particles act as seeds allowing nucleation and growth of the apatite crystals. As a result of this protocol, a 10–1000 μm large, nano-to-submicron porous CPC-HA microspheres matrix encapsulating the drug material is achieved. In the last Stage 4 of the process (FIG. 3), a thin film of BM-HA may be deposited on the microsphere surface for additional encapsulation. FIG. 4 is SEM micrograph of two CPC-HA microspheres, ~20 um large (a) and ~300 um large (b), produced according to the above process (BM-HA is not present on these microspheres). By changing the content of HA seeds in the microspheres, crystallinity (and thus resorption rate in physiological environment) of the resulting CPC-HA may be varied. This is illustrated in FIG. 5, showing microcrystalline (a) and amorphous (b) structure of CPC-HA (these are confirmed by XRD and FTIR data).

Figure 6A:
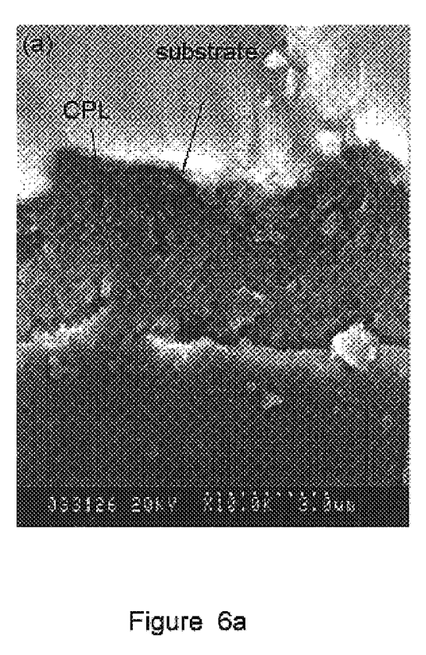
FIGS. 6(a) and 6(b) illustrate biomimetic hydroxyapatite (BM-HA) film deposits, termed CPL, for calcium phosphate layer, on SG-HA substrate of low crystallinity (a) and of high crystallinity (b).
Figure 6B:
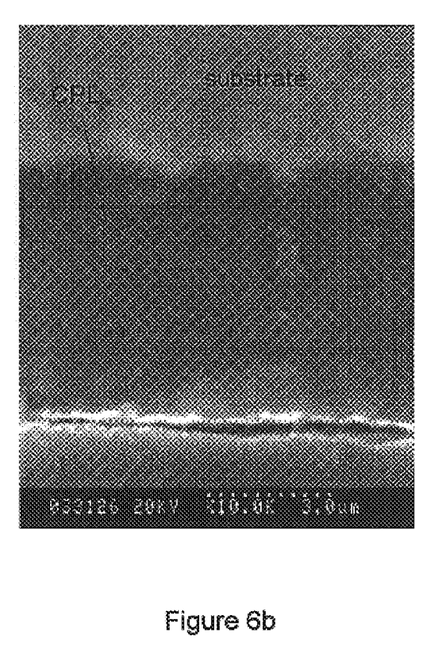

The coatings and microspheres are processed such as to encapsulate secondary materials within the open and closed porosity of HA, the secondary material being preferably for therapeutical use, such as drugs, proteins, genes, DNA and the like. We have demonstrated that a direct, in-situ encapsulation, and subsequent controlled release of therapeutically active agents from such apatite coatings and microspheres can be achieved. Both the coatings and microspheres are designated for side-effects free, long-term, targeted, controlled release and delivery of drugs, proteins, DNA, and others. The disclosed process addresses the issue of drug delivery through encapsulation (entrapment within the structure) rather than impregnation of drugs into HA matrix. Thus, the drug release is linked to resorption of the HA matrix, rather than leaching from the matrix. Materials process engineering has been developed to control structure of HA for drug encapsulation, and therefore to control the HA resorption and drug or gene delivery process. The bio-resorbable HA for drugs encapsulation is designed and processed to release the drug as a result of gradual resorption of the matrix, rather than leaching of the drug from open porosity of the matrix. The additional BM-HA encapsulation film grown on SG-HA coated substrate is shown in SEM micrographs in FIG. 6. The biomimetic hydroxyapatite (BM-HA) film deposits, termed CPL here for calcium phosphate layer, are shown on SG-HA substrate of low crystallinity (a) and high crystallinity (b).

In the specification and the claims, it is understood that when appropriate, the term "calcium phosphate" (CaP) is used generically and includes minerals such as hydroxyapatite, dicalcium phosphate, tricalcium phosphate and tetracalcium phosphate.

We disclose multilayer biocompatible/bioactive functionally graded calcium phosphate in two forms: (i) coatings on variety of substrates, typically stainless steel or titanium, and (ii) self-supporting microspheres. Two types of coatings are deposited. The first coating directly on the metal surface is a thin film (0.2–0.5 μm) of dense, highly crystalline HA produced through sol-gel technology at elevated temperatures, about 400 C. This coating serves several purposes: (i) to screen the metal surface from the surrounding tissue; (ii) to provide high-adhesion and nucleation surface for the second CPC-HA coating. The second coating is thicker, porous, film (10–1000 μm) of HA processed at room temperature. The goal is to achieve rapid formation of an adhesive apatite layer through dissolution-precipitation mechanism similar to setting of calcium phosphate cements (CPC). By adding drugs with various concentrations into the CPC colloidal suspension, a direct, in-situ encapsulation, and subsequent controlled release of therapeutically active agents from the apatite coatings is achieved. The varying degree of crystallinity of the coating and multi-step coating/impregnation techniques is used to control and customize the CPC-HA resorption process, and thus the rate of drug release from the CPC-HA matrix. Interfacial examination (FIG. 2a) shows that the CPC-HA coating is in intimate contact with the underlying SG-HA thin layer. The key feature of the present invention is therefore that the pre-coated thin SG-HA film acts as a template for the nucleation and growth of room-temperature precipitated apatite in the CPC-HA coating. Such mechanism allows a significant interfacial bonding to develop between the thin SG-HA and the thick CPC-HA, as observed.

FTIR spectra of the resulting CPC-HA, FIG. 2b, suggest disorder of the crystal structure, attributed to poor symmetry of $PO_4$ tetrahedra. Effectively, the resulting CPC-HA is amorphous, or very fine, poorly crystalline, non-stoichiometric, easily resorbable apatite similar to that found in bone mineral, i.e. $Ca_9(PO_4)_{5-x-y}(CO_3)_y(HPO_4)_x(OH)_{1-y/3}$. This CPC-HA had a porosity of about 45% and an average pore size of about 16 nm. The nanopores in the CPC-HA physically immobilize encapsulated biomolecules of similar dimension, such that dissolution of the CPC-HA matrix is responsible for the release kinetics (rather than simply desorption and leaching, as disclosed in previous art). This offers additional mode of drug/gene release control, e.g. through adjustment of the resorption rate (i.e. adjustment of crystallinity) of the CPC-HA microspheres or coatings.

We also disclose here the newly discovered approach to achieve the active CaP microsphere, capable to encapsulate any type of drug or biomolecule which can be dispersed in organic liquids or water. The approach combines spheroidization of calcium phosphate cement (CPC) slurry, followed by incubation to precipitate HA phase, FIGS. 3, 4. The CPC-HA microspheres have a poorly crystalline calcium-deficient apatitic structure, similar to that of natural (bone) apatite, and identical to that determined for the thick CPC-HA coatings grown on SG-HA substrates. The microstructure (i.e. in particular crystallinity and nano-porosity) of the apatite granules can be tailored by adjusting the concentration of the seeding HA sintered sub-micron powder. The greater amount of the seeds, the finer the resulting microstructure results in the matrix phase. The examples of microstructures of crystalline (a) and amorphous (b) CPC-HA produced in our laboratory through changing seeding and process parameters are shown in FIG. 5. The key feature of the present invention is that the microspheres are shaped at room temperature, and CPC-HA nucleated and grown also at room temperature, encapsulating the designated organic material, e.g. drug or protein.

In order to achieve better control of drug release, additional film of BM-HA will be deposited on the surface of the microspheres, as illustrated in FIG. 3 (Stage 4), and also FIG. 6. We have demonstrated previously that excellent quality BM-HA can be grown through solution-precipitation on hydroxyapatite films. BM-HA can be grown on surface of CPC-HA microspheres for final, long term encapsulation.

EXAMPLES

Example 1
CPC-HA/SG-HA Coatings on Stainless Steel

Stainless steel metallic substrates (316 L) were coated with a 0.6–0.8 μm thin layer of apatite (SG-HA) using the recently developed sol-gel technique. Specifically, the sol-gel process for preparing a crystallized hydroxyapatite, comprises: (a) hydrolysing a phosphor precursor (phosphite) in a water based medium; (b) adding a calcium salt precursor to the medium after the phosphite has been hydrolysed to obtain a calcium phosphate gel such as a hydroxyapatite gel; (c) depositing the gel on the substrate through dip coating, and (c) calcining the film to obtain crystallized hydroxyapatite, at 400° C. for 20 min. An inorganic colloidal slurry containing calcium phosphate precursor $Ca(OH)_2$ and calcium phosphate salt monocalcium phosphate anhydrate, was ball milled in ethanol. The two starting inorganic ingredients had particle size 0.3–2 μm and 0.5–4 μm, respectively. The initial Ca/P ratio in the slurry was kept at 1.5. As dissolution and precipitation are the principal mechanisms for apatite development in such system, 5 wt % of submicron, crystalline hydroxyapatite powder was used as seeds for heterogeneous nucleation of CPC-HA. The thin film SG-HA surface-modified sample was dip coated in the ethanol suspension of the precursors. After single dip coating, an approximately 30 μm thick layer of porous precursor powder mixture developed on the substrate due to rapid evaporation of ethanol. Due to colloidal nature of the precursors slurry, the thick film develops sufficient structural integrity (i.e. strength and hardness) to accept the next processing step. In this step, the film is exposed to sodium phosphate water-based solution (0.25 M), which is allowed to soak into the open pores of the film, and then placed in an incubator at 37° C., 100% relative humidity, for 24 h. During incubation, the colloidal precursors react with the phosphate liquid and precipitate HA. Microstructure of the resulting CPC-HA thick film is shown in FIG. 5a. The pull adhesion test performed on the coatings according to ASTM C-633 standard revealed adhesion strength of the thick CPC-HA film to the thin SG-HA film of 6.1±1.2 MPa (test on 6 specimens with ~20 μm thick coating). This bonding strength is greater than the tensile strength of bulk CPC-HA reported in literature, which is generally <2 MPa. The fracture mode was predominantly at the SG-HA/CPC-HA interface, indicating that the interface is the weakest link region. This CPC-HA had a porosity of about 45% and an average pore size of about 16 nm. Macrograph of the coated sample is shown in FIG. 1b. Micrograph of the coating interface is illustrated in FIG. 2a, and FTIR spectrum in FIG. 2b.

Example 2
CPC-HA Coatings on Stainless Steel

Stainless steel metallic substrates (316 L) free of intermediate SG-HA film were coated with CPC-HA, as described in Example 1. During HA incubation period, the coating spontaneously separated from the substrate, as illustrated in FIG. 1a. Obviously, the CPC-HA coating did not bond to the metallic substrate, i.e. bonding strength was zero MPa. Other properties of the coating, that is phase content and porosity, was similar to that obtained in Example 1.

Example 3
BM-HA/SG-HA Coatings on Stainless Steel

Stainless steel metallic substrates (316 L) were coated with a 0.6–0.8 μm thin layer of apatite (SG-HA) as described in Example 1. One group of samples was annealed at 400° C. for 20 min to achieve crystalline SG-HA(C) film and another group at 375° C. for 60 min to achieve amorphous SG-HA(A) film. These films were used as nucleation site for precipitation of BM-HA film. The SG-HA coated samples were immersed into "simulated body fluid" (SBF) of ionic composition (in units of mmol/l) 142 $Na^+$, 5.0 $K^+$, 2.5 $Ca^{2+}$, 1.5 $Mg^{2+}$, 103 $Cl^-$, 25 $HCO_3^{3+}$, 1.4 $HPO_4^{2-}$, and 0.5 $SO_4^{2-}$. The SBF was buffered at pH 7.4 with tris(hydroxymethyl)-aminomethane and HCl. This in-vitro static deposition (i.e. the SBF was not renewed during the deposition period) at ~24° C. produced good quality, dense 3–5 μm thick BM-HA film deposits on flat SG-HA substrates, as illustrated in FIG. 6. The crystalline SG-HA(C) film, FIG. 6b, coated with dense BM-HA, whereas amorphous SG-HA(A) film, FIG. 6a, coated with porous BM-HA. The properties of the underlying SG-HA surface modification film can be used to vary the properties, e.g. porosity, of the nucleated and deposited top BM-HA film.

Example 4
CPC-HA/SG-HA Coatings with Encapsulated Drug

Figure 7:
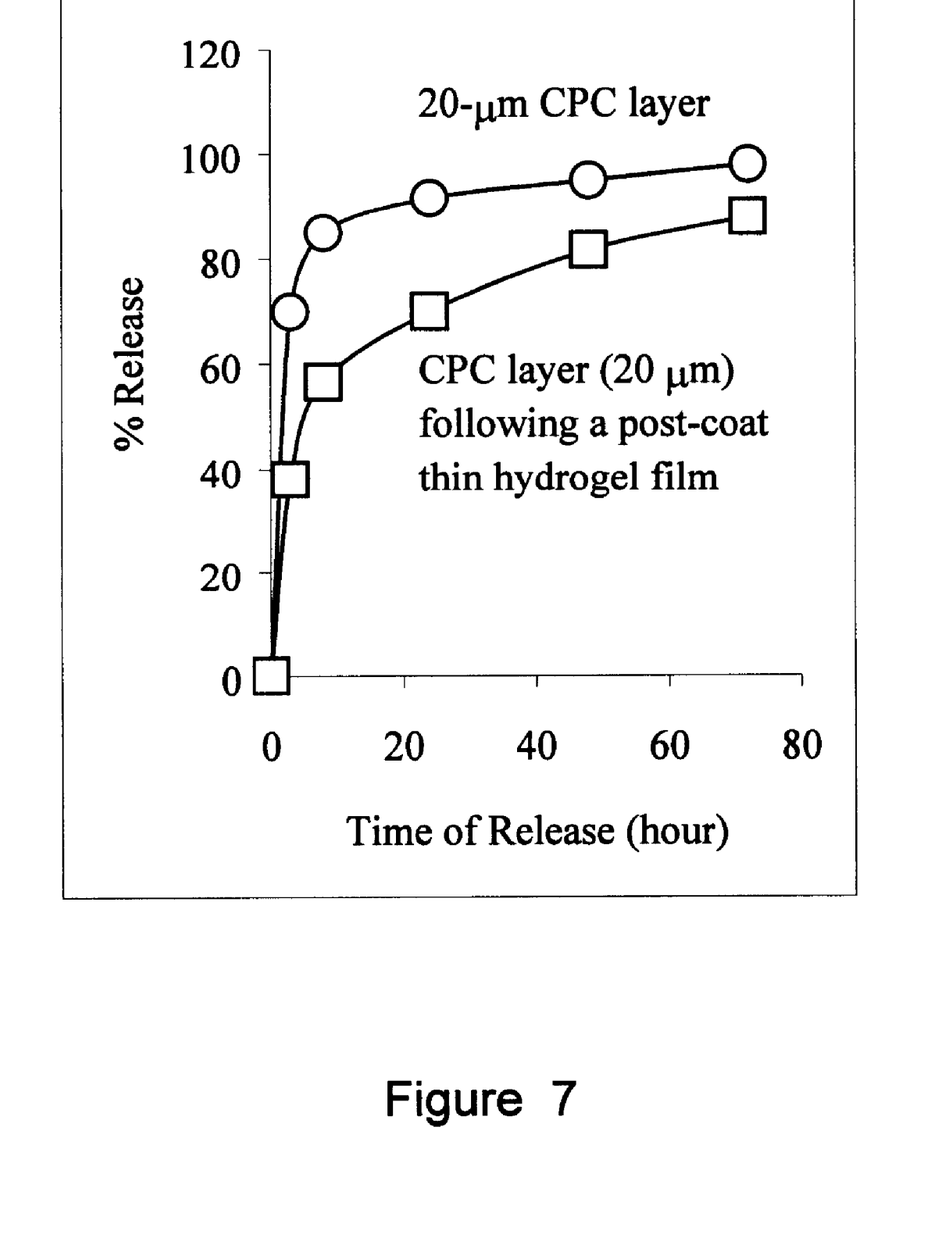
FIG. 7 illustrates a plot of % Release vs. Time of Release (hours) for the HA-CPC coating with 5% of amethopterin drug encapsulated.

Stainless steel metallic substrates (316 L) were coated with CPC-HA/SG-HA coatings as described in Example 1. In order to assess the possibility of use of CPC-HA for controlled drug release, amethopterin (Sigma Chemicals, USA) was employed as a model drug, in an amount of 5% based on solid phase content of CPC-HA precursors. The drug was mixed with the colloidal suspension of the precursors, before dip coating was performed. All other procedures, e.g. incubation, were performed as in Example 1. During incubation period, 20 µm thick CPC-HA coating precipitated encapsulating the drug molecules within the nanopores of the crystallizing HA. After encapsulation, a drug release study was conducted by immersion of the substrates into 20 ml of phosphate buffer saline (PBS, pH=7.4) at constant ratio of (CPC coating weight)/(volume of PBS) of 1 mg/ml. A reference sample coated with hydrogel film was also tested for drug release kinetics. The hydrogel film was prepared by dipping the CPC-HA layer containing the drug into a polymer solution containing 3% polyvinyl alcohol. After drying, the weight gain of the ~20 mg CPC-HA layer due to the additional hydrogel coating was ~0.5 mg, corresponding to the content of polymer film in the CPC-HA matrix of about 2.5%. The samples of PBS liquid with released drug were periodically taken out (i.e. entire liquid was emptied) and refilled with the same amount of 20 ml of PBS. The drug concentration in the supernatant was determined via an UV-Visible spectroscopy. FIG. 7 illustrates the drug release kinetics for the time period of 3 days, for both types of drug-loaded CPC-HA. Although a burst effect was detected for both coatings over the initial period of about 8 h, a slower release is evident for the sample post-coated with hydrogel. A linear relationship was obtained between the amount of drug released and $(time)^{1/2}$ for the release time greater than 8 h. The sustain release period for 8 to 60 h is well described by Fick's law of diffusion. The release kinetics is modified due to the presence of a post-coated thin hydrogel film, suggesting a decreased diffusivity of the drug molecules. However, the burst effect can offer an advantage in the early period after orthopedic/dental surgeries if anti-inflammatory agents were incorporated into the implant devices to avoid acute or severe inflammatory response.

Example 5

CPC-HA Microspheres

An inorganic colloida slurry containing $Ca(OH)_2$ and monocalcium phosphate anhydrate, is ball milled in ethanol, at Ca/P ratio=1.5 (this stage of the process is similar to CPC-HA coatings processing, as described in Example 1). As dissolution and precipitation are the principal mechanisms for apatite development in such system, small amount (2 wt %) of crystalline HA powder is added to the slurry as seeds for heterogeneous nucleation of HA. Microstructure, in particular nano-porosity, of the apatite granules is tailored by adjusting concentration of the seeding HA sintered submicron powder, in the range 1–10 wt %. The greater amount of the seeds, the finer the resulting microstructure of the CPC-HA matrix phase. The slurry is atomized and spray dried to produce spheres due to rapid evaporation of ethanol, as illustrated in FIG. 3a. Narrow distribution of the microsphere size can be achieved by varying spray parameters (such as spray pressure; slurry viscosity and concentration), with average granular size achievable in the range 10–1000 µm diameter. Any secondary dopant, e.g. drug material, is entrapped in the pores of the sphere at this processing stage, as in Example 4, and also as schematically illustrated in FIG. 3b. The colloidal nature of the precursors sol allows a relatively strong bond to develop within the flash-dried precursor microsphere, Stage 1, FIG. 3b. Subsequently, the microspheres were exposed to sodium phosphate water-based solution (0.25 M) and placed in an incubator at 37° C., 100% relative humidity for 24 h, Stage 2. A poorly crystalline, calcium-deficient apatitic structure develops within the microsphere in this process, similar to that of naturally occurring apatite, as described above for the coatings, Stage 3. A poorly crystalline, calcium-deficient apatitic structure develops within the microsphere in this process, similar to that of naturally occurring (i.e. bone) apatite. The mineralization process in Stage 3 can be expressed as a result of interaction between $Ca(OH)_2$ and $Ca(HPO_4)_2$ in the film exposed to sodium phosphate solution:

The microstructures of the resulting small (~20 µm) and large (~300 µm) microspheres are presented in FIG. 5. In the final Stage 4 of the process illustrated in FIG. 3b, a thin, dense film of BM-HA may be deposited on surface of the porous HA macrosphere for long-term encapsulation function. To achieve this, HA-CPC spheres with drug encapsulated in its nanopores are immersed into simulated body fluid as described in Example 3.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

REFERENCES

1. L. L. Hench, J. Am. Ceram. Soc., 74, 1487–1510 (1991).
2. C. Ohtsuki, T. Kokubo, and T. Yamamuru, J. Non-Cryst. Solids, 143, 84–92 (1992).
3. P. Ducheyne, S. Radin, and K. Ishikawa, in Bone-Bonding Biomaterials, P. Duchenye, T. Kokubo, and C. A. van Blitterswijk (eds), Reed Healthcare Communications, Leiderdrop, pp. 213–18 (1992).
4. D. M. Liu, H. M. Chou, and J. D. Wu, J. Mater. Sci. Mater. Med., 5, 147–153 (1994).
5. K. de Groot, R. G. T. Greesink, C. P. A. T. Klein, and P. Serekian, J. Biomed. Mater. Res., 21, 1375–1381 (1987).
6. C. M. Lopatin, V. Pizziconi, T. L. Alford, and T. Laursen, Thin Solid Films, 326, 227–232 (1998).
7. C. S. Chai, B. Ben-Nissan, S. Pyke, and L. Evans, Mater. Manuf. Processes, 10, 205–216 (1995).
8. D. M. Liu, T. Troczynski, and W. J. Tseng, Biomaterials (in press, 2001).
9. H. B. Wen, J. G. C. Wolke, J. R. de Wijn, Q. Lin, F. Z. Cui, and K. de Groot, Biomaterials, 18, 1471–78 (1997).
10. A. A. Campbell, G. E. Fryxell, J. C. Linehan, and G. L. Graff, J. Biomed. Mater. Res., 32, 111–118 (1996).
11. Y. Abe, T. Kokubo, and T. Yamamuru, Materials in Madicine, 1, 233–238 (1990).
12. H. M. Kim, Y. Kim, S. J. Park, C. rey, H. M. Lee, M. J. Glimcher, and J. S. Ko, Biomaterials, 21, 1129 (2000).
13. H. B. Wen, J. R. de Wijn, F. Z. Cui, and K. de Groot, J. Biomed. Mater. Res., 41, 227–36 (1998).
14. S. Lin and A. A. Campbell, U.S. Pat. No. 5,958,430, 1999.
15. L. C. Chow, S. Takagi, P. D. Constantino, and C. D. Friedman, Mat. Res. Soc. Symp. Proc., 179, 3–24, 1991.
16. B. R. Constantz, I. C. Ison, M. T. Fulmer, R. D. Doster, S. T. Smith, M. vanWangoner, J. Ross, S. A. Goldstein, J. B. Jupiter, and D. I. Rosenthal, Science 267, 1796 (1995).
17. F. C. Driessens, M. G. Boltong, O. Bermudez, J. A. Planell, M. P. Ginebra, and E. Fernandez, Materials in Medicine, 5, 164 (1994).
18. L. M. Ellerby, C. R. Nishida, F. Nishida, S. A. Yamanakas, B. Dunn, S. J. Valentine, and J. I. Zink, Science, 255, 1113 (1992).

19. D. M. Liu and I. W. Chen, Acta Materialia 47, 4535 (1999).

What is claimed is:

1. A process for preparing a calcium phosphate coating composition which comprises:
   (a) dispersing a homogenization of monocalcium phosphate $Ca(H_2PO_4)_2$ and calcium hydroxide $Ca(OH)_2$ precursors and a drug or protein in a substantially water-free medium to form a paste or viscous slurry of precursors;
   (b) depositing and drying the slurry of precursors on the surface of a calcium phosphate substrate;
   (c) admixing a water-based solution of phosphate ions in the slurry to produce a mixture; and
   (d) incubating the resulting mixture in a humid environment at a temperature of 20–50° C. to dissolve the precursors and precipitate a calcium phosphate coating composition.

2. A process as claimed in claim 1 wherein the calcium phosphate coating composition is hydroxyapatite.

3. A process as claimed in claim 1 wherein the Ca/P atomic ratio in the precursors mixture is in the range of 1.2–1.67 and the mixture has a solids concentration of 30–70 vol %.

4. A process as claimed in claim 1 wherein the substantially water-free medium is an alcohol.

5. A process as claimed in claim 4 wherein the alcohol is ethyl alcohol, methyl alcohol or propyl alcohol.

6. A process as claimed in claim 1 wherein the water-based solution of phosphate ions is sodium phosphate and the humid environment is 50% to 100% Relative Humidity.

7. A process as claimed in claim 1 wherein a crystalline hydroxyapatite powder is added to the precursors slurry to promote crystallization of hydroxyapatite calcium phosphate phase during the incubation period.

8. A process as claimed in claim 1 wherein a drug or protein is added to the precursors slurry for encapsulation during crystallization of the hydroxyapatite calcium phosphate phase during the incubation period.

9. A process as claimed in claim 1 wherein the calcium phosphate substrate is a thin film of hydroxyapatite coating deposited on a metallic substrate using sol-gel process.

10. A process as claimed in claim 1 wherein the precipitated calcium phosphate phase is exposed to a solution supersaturated with $Ca^{2+}$ and $PO_4^{3-}$ ions to provide a coating of biomimetic hydroxyapatite film on the precipitated calcium phosphate phase.

11. A process as claimed in claim 8 wherein the precipitated calcium phosphate phase is exposed to a solution Supersaturated with $Ca^{2+}$ and $PO_4^{3-}$ ions to provide a coating of biomimetic hydroxyapatite film on the precipitated calcium phosphate phase.

12. A calcium phosphate coating composition prepared according to the process of claim 1.

13. A calcium phosphate phase-substrate prepared according to claim 9.

* * * * *